US006284496B1

(12) United States Patent
Litman et al.

(10) Patent No.: US 6,284,496 B1
(45) Date of Patent: *Sep. 4, 2001

(54) DNA VECTOR FOR DETERMINING THE PRESENCE OF OUT-OF-READING-FRAME MUTATIONS

(75) Inventors: Gary W. Litman, Clearwater; Noel A. Hawke, St. Petersburg; Robert N. Haire, Clearwater, all of FL (US); Scott J. Strong, Keene, NH (US)

(73) Assignee: University of South Florida, Tampa, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/165,934

(22) Filed: Jan. 2, 1998

Related U.S. Application Data

(60) Provisional application No. 60/060,916, filed on Oct. 3, 1997.

(51) Int. Cl.[7] ................................................. C12P 19/34
(52) U.S. Cl. .................... 435/91.2; 435/69.1; 435/172.3; 435/252.3; 435/320.1; 536/24.1; 935/22; 935/23; 935/33; 935/52; 935/55; 935/56; 935/66
(58) Field of Search ................................. 435/91.2, 69.1, 435/172.3, 252.3, 320.1; 536/24.1; 935/22, 23, 33, 52, 55, 56, 66

(56) References Cited

U.S. PATENT DOCUMENTS

| | | |
|---|---|---|
| 3,791,932 | 2/1974 | Schuurs et al. . |
| 3,839,153 | 10/1974 | Schuurs et al. . |
| 3,850,578 | 11/1974 | McConnell . |
| 3,850,752 | 11/1974 | Schuurs et al. . |
| 3,853,987 | 12/1974 | Dreyer . |

(List continued on next page.)

OTHER PUBLICATIONS

Varesco et al. Cancer Research. vol. 53, pp. 5581–5584, Dec. 1, 1999.*

Bozdech, et al., 1996. Cloning and sequence analysis of a novel member of the ATP–binding cassette (ABC) protein gene family from Plasmodium falciparum. Mol. Biochem. Parasitol. 81:41–51. (not available—will mail in).

Chalfie, et al., 1994. Green Fluorescent Protein as a Marker for Gene Expression. Science 263:802–805.

Claverie, 1995. Detecting Frame Shifts by Amino Acid Sequence Comparison. J. Mol. Biol. 234:1140–1157.

Crameri, et al., 1996. Improved green fluorescent protein by molecular evolution using DNA shuffling. Nat. Biotechnol. 14:315–319. (not available—will mail in).

Fichant and Quentin, 1995. A frameshift error detection algorithm for DNA sequencing projects. Nucleic Acid Res 23(15):2900–2908.

(List continued on next page.)

*Primary Examiner*—W. Gary Jones
*Assistant Examiner*—Janell E. Taylor
(74) *Attorney, Agent, or Firm*—Kohn & Associates

(57) ABSTRACT

A DNA expression vector for positively selecting in-frame or out-of-reading-frame mutations in DNA sequences to be tested comprising a promotor operatively linked to an expressible reporter gene through a linkage sequence is disclosed. The linkage sequence includes at least two restriction sites and an engineered frameshift mutation. In an embodiment the frameshift is established by complementary sequences SEQ ID Nos:1 and 2. The expressible reporter gene is expressed as a fusion product including a green fluorescent protein and the promoter can be lacZ and inducible in *E. coli*.

8 Claims, 2 Drawing Sheets

U.S. PATENT DOCUMENTS

| | | |
|---|---|---|
| 3,867,517 | 2/1975 | Ling . |
| 3,879,262 | 4/1975 | Schuurs et al. . |
| 3,901,654 | 8/1975 | Gross . |
| 3,935,074 | 1/1976 | Rubenstein et al. . |
| 3,984,533 | 10/1976 | Uzgiris . |
| 3,996,345 | 12/1976 | Ullman et al. . |
| 4,034,074 | 7/1977 | Miles . |
| 4,098,876 | 7/1978 | Piasio et al. . |
| 4,666,828 | 5/1987 | Gusella . |
| 4,683,202 | 7/1987 | Mullis . |
| 4,801,531 | 1/1989 | Frossard . |
| 4,879,219 | 11/1989 | Wands et al. . |
| 5,011,771 | 4/1991 | Bellet et al. . |
| 5,162,227 | 11/1992 | Cormier . |
| 5,192,659 | 3/1993 | Simons . |
| 5,272,057 | 12/1993 | Smulson et al. . |
| 5,281,521 | 1/1994 | Trojanowski et al. . |
| 5,422,266 | 6/1995 | Cormier et al. . |
| 5,491,084 | 2/1996 | Chalfie et al. . |
| 5,538,885 | 7/1996 | Hollis et al. . |
| 5,545,531 | 8/1996 | Rava et al. . |
| 5,665,565 * | 9/1997 | Petri, Jr. et al. ............... 435/69.1 |

OTHER PUBLICATIONS

Fire, et al., 1990. A modular set of lacZ fusion vectors for studying gene expression in *Caenorhabditis elegans*. Gene 93:198–198.

Hardy and Duff, 1993. Heterogeneity in Alzheimer's Disease. Ann.Med. 25:437–440. (not available—will mail in).

Hawke et al., 1996. Improvements in short primer PCR based identification of novel IgSF members. Suncoast Biomolecular Science Conference, 34, Abstract P–2.

Kain et al., 1995. Green Fluorescent Protein as a Reporter of Gene Expression and Protein Localization. BioTechniques 19:650–655.

Kahn et al., 1995. Design of a selectable reporter for the detection of mutations in mammalian simple repeat sequences. Carcinogenesis 16(5):1223–1228.

Kim, et al., 1996. Characterization of the PEST family protein tyrosine phosphatase BDP1. Oncogene 13:2275–2279. (not available—will mail in).

Marwood, et al., 1995. *Escherichia coli* lacZ strains engineered for detection of frameshift mutations induced by aromatic amines and nitroaromatic compounds. Carcinogenesis 16(9):2037–2043.

Misteli and Spector, 1997. Applications of the green fluorescent protein in cell biology and biotechnology. Nature Biotechnology 15:961–964. (not available—will mail in).

Partula, et al., 1995. Structure and diversity of the T cell antigen receptor b–chain in a teleost fish. J. Immunol. 155:699–706. (not available—will mail in).

Prasher, et al., 1992. Primary structure of the Aequorea victoria green–fluorescent protein. Gene 111:229–233. (not available—will mail in).

Rast, et al., 1997. a, b, g, and d T cell antigen receptor genes arose early in vertebrate phylogeny. Immunity 5:1–11. (not available—will mail in).

Rast, et al., 1995. Identification and characterization of T–cell antigen receptor related genes in phylogenetically diverse vertebrate species. Immunogenetics 42:204–212. (not available—will mail in).

Rast and Litman, 1994. T cell receptor gene homologs are present in the most primitive jawed vertebrates. Proc. Natl. Acad. Sci. USA 91:9248–9252. (not available—will mail in).

Yang et al., 1996. The molecular structure of green fluorescent protein. Nature Biotechnology 14:1246–1251. (not available—will mail in).

Yoshihara, et al., 1994. BIG–1: a new TAG–1/F3–related member of the immunoglobulin superfamily with neurite outgrowth–promoting acitivity. Neuron 13:415–426. (not available—will mail in).

Varesco, et al., 1993. A rapid screening method to detect nonsense and frameshift mutations: Identification of Disease–causing APC Alleles. Cancer Research 53:5581–5584.

Fodor et al, "Multiplexed biochemical assays with biological chips", *Nature* 364:555–556 (1993).

Kawasaki ES. Amplification of RNA. In: PCR protocols: A Guide to Methods and Applications, Innis MA, Gelfand DH, Sninsky JJ, White TJ, eds. Academic Press, 1990, pp21–27.

Lichter et al., "High–resolution mapping of human chromosome 11 by in situ hybridization with cosmid clones" *Science* 247:64–69 (1990). (not available—will mail in).

Orita et al. Detection of polymorphisms of human DNA by gel electrophoresis as single–strand conformation polymorphisms. Proc Natl Acad Sci USA 1989; 86:2766–2770.

Pease et al., "Light–generated oligonucleotide arrays for rapid DNA sequence analysis", *Proc. Natl. Acad. Sci. USA* 91(11): 5022–5026 (1994).

Testoni et al., 1996. Blood 87:3822 (not available—will mail in).

Hawke et al., Vector for Positive Selection of In–Frame Genetic Sequences, *Biotechniques* (1997) 23:619–621.

* cited by examiner

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:1:

GATCGATATC TCGAGT                                16

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:2:

CTAGACTCGA GATATCGATC TGCA                      24

DNA VECTOR FOR DETERMINING THE PRESENCE OF OUT-OF-READING-FRAME MUTATIONS

CROSSREFERENCE TO RELATED APPLICATIONS

This application claims priority from U.S. Ser. No. 60/060,916, filed Oct. 3, 1997.

GOVERNMENT SUPPORT

Research in this application was supported in part by grants from the National Institutes of Health R38 AI23338 and R03 AI40137. The Government has certain rights in the invention.

BACKGROUND OF THE INVENTION

1. Field of the Invention

The present invention relates to recombinant DNA technology and in particular to a method of detecting frameshift mutations or assuring an in-frame coding sequence in a nucleic acid sequence. The present invention also provides a vector for use in the method.

2. Description of Related Art

Changes in the reading frame of a gene including additions or subtractions of nucleotides, i.e. frameshift, generally leads to termination of translation and/or formation of truncation products often through generation of new stop codons and can also be referred to as an out-of-reading-frame mutation. For example, cystic fibrosis, Duchenne muscular dystrophy, fragile X, Huntington's disease, Alzheimer's disease (Hardy and Duff, 1993), Ataxia Telangiectasia, Marfan syndrome, neurofibromatosis, familial adenomatous polyposis coli (Varesco et al, 1993) and osteogenesis imperfecta are diseases that can result from a frameshift mutation in a particular susceptibility gene.

Identification of such mutations can be undertaken utilizing RFLP, in situ hybridization, Southern blotting, single strand conformational polymorphism, PCR amplification and DNA-chip analysis using specific primers. (Kawasaki, 1990; Kahn et al., 1995; Lichter et al, 1990; Marwood et al., 1995; Orita et al, 1989; Fodor et al., 1993; Pease et al., 1994; U.S. Pat. No. 5,545,531; PCT applications WO98/28444). The methods now available fall into six classes: electrophoretic mobility alteration methods such as single-strand conformational polymorphism (SSCP), restriction enzyme fingerprinting (REF); mismatch cleavage methods; mismatch recognition methods; direct sequencing methods and protein truncation tests (see Genome Analysis Volume 2, pages 288–289 for a more detailed listing).

In general these methods require sophisticated and expensive equipment and in several instances require that the frameshift mutations be known so that appropriate primers or chip sequences can be prepared. Additionally, most of these methods require amplification by PCR with the inherent problems of PCR as discussed herein below. Direct sequencing does not require that the frameshift mutation be known but does generally require automated sequencing equipment and skilled technical support. Further detection of systemic errors are also needed (Fichant and Quentin, 1995; Claverie, 1993). These methods do not lend themselves to rapid, inexpensive screening or scanning particularly for new out-of-reading-frame mutations. Additionally, several of these techniques, such as SSCP, tend to provide an unacceptably high false positive rate. For example, a polymorphism which causes what can be termed a neutral change in the DNA code and without pathogenic consequences will be identified even though it is not a frameshift.

The Varesco et al, 1993 reference provides a vector system to detect specific frameshift mutations in the APC gene consisting of a promotor, out-of-frame insert and β-galactosidase as the reporter gene. However this method is probably limited to screening for known mutations in familial adenomatous polyposis coli (APC) due to the construction of the vector. Further, the detection of β-galactosidase as a reporter gene under the selected promotor requires subjective qualitative differentiation so that even with a frameshift in place it is possible to obtain false results. Further as indicated in the reference there is no consistency between plates. Additionally, the presence of a frameshift produces an intermediate color which can be difficult to score.

Therefore a method is needed for rapidly and reliably detecting out-of-reading-frame mutations such as deletions, missense, nonsense and stop codons in nucleic acid sequences that does not suffer from the limitations of the methods described above. It would be useful to have a method for positively selecting among samples those containing coding sequences which have a correct reading frame that is rapid, simple and inexpensive so that susceptibility genes for both known and de novo mutations can be screened.

Polymerase chain reaction (PCR)-based approaches are becoming increasingly important for the identification of members of extended multigene families as well as homologous gene structures present in phylogenetically divergent species (Bozdech et al., 1996; Kim et al., 1996; Rast et al., 1994; Yoshihara et al., 1994). Many of these approaches rely on the use of highly degenerate primers and/or reduced priming stringencies that can generate a broad range of products, including significant numbers of amplification products that contain frameshift(s) and/or termination codon (s) which are referred to as amplification artifacts. Recently, Applicants introduced the use of short, minimally degenerate primers complementing conserved structural motifs for PCR amplification of homologs of antigen binding receptor genes in phylogenetically diverse species (Partula et al., 1995; Rast et al., 1994, 1995, 1997). This approach is also associated with the generation of amplification artifacts that require DNA sequencing to be distinguished from products that warrant further study. In order to analyze DNA sequences, polymerase chain reaction (PCR) is routinely used. However, in addition to the problems associated with the techniques listed herein, amplification artifacts are sometimes found in PCR products which usually result from errant priming of non-coding sequences which have multiple stop codons, but also can change an open reading frame (in-frame) to an out-of-frame sequence or the converse. It would therefore be useful to have a method to rapidly screen PCR products to ensure open reading frame continuity, that the PCR amplification had not introduced these types of errors. Direct sequencing of the PCR products can be undertaken to determine this, but it would be useful to have a more rapid, less expensive, screening method.

SUMMARY OF THE INVENTION

According to the present invention, a DNA expression vector for positively selecting out-of-reading-frame mutations in a DNA sequence to be tested comprising a promotor operatively linked to an expressible reporter gene through a linkage sequence is disclosed. The linkage sequence includes at least two restriction sites and an engineered frameshift mutation. In one embodiment the frameshift is established by the complementary sequences SEQ ID Nos:1 and 2. The expressible reporter gene is expressed as a fusion product as described herein and in an embodiment including a green fluorescent protein. In an embodiment, the promoter can be lacZ and inducible in E. coli.

The present invention further provides a method to evaluate PCR products for open reading frame continuity, i.e. to ensure that there are no amplification artifacts. The method includes cloning the PCR product into the DNA expression vector of the present invention and transforming a microorganism with the recombinant DNA vector. Expression of the reporter gene is induced and the presence of the reporter gene product is assayed. The reporter gene product is produced if the reading frame is open, that is the PCR product does not contain a stop codon or other frameshifts and in screening application does contain out-of-reading-frame mutations including frameshifts and stop codons in DNA sequences. In screening the vector allows for positively selecting out-of-reading-frame mutations including frameshifts and stop codons in DNA sequences which need to be tested for frameshifts and/or stop codons.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
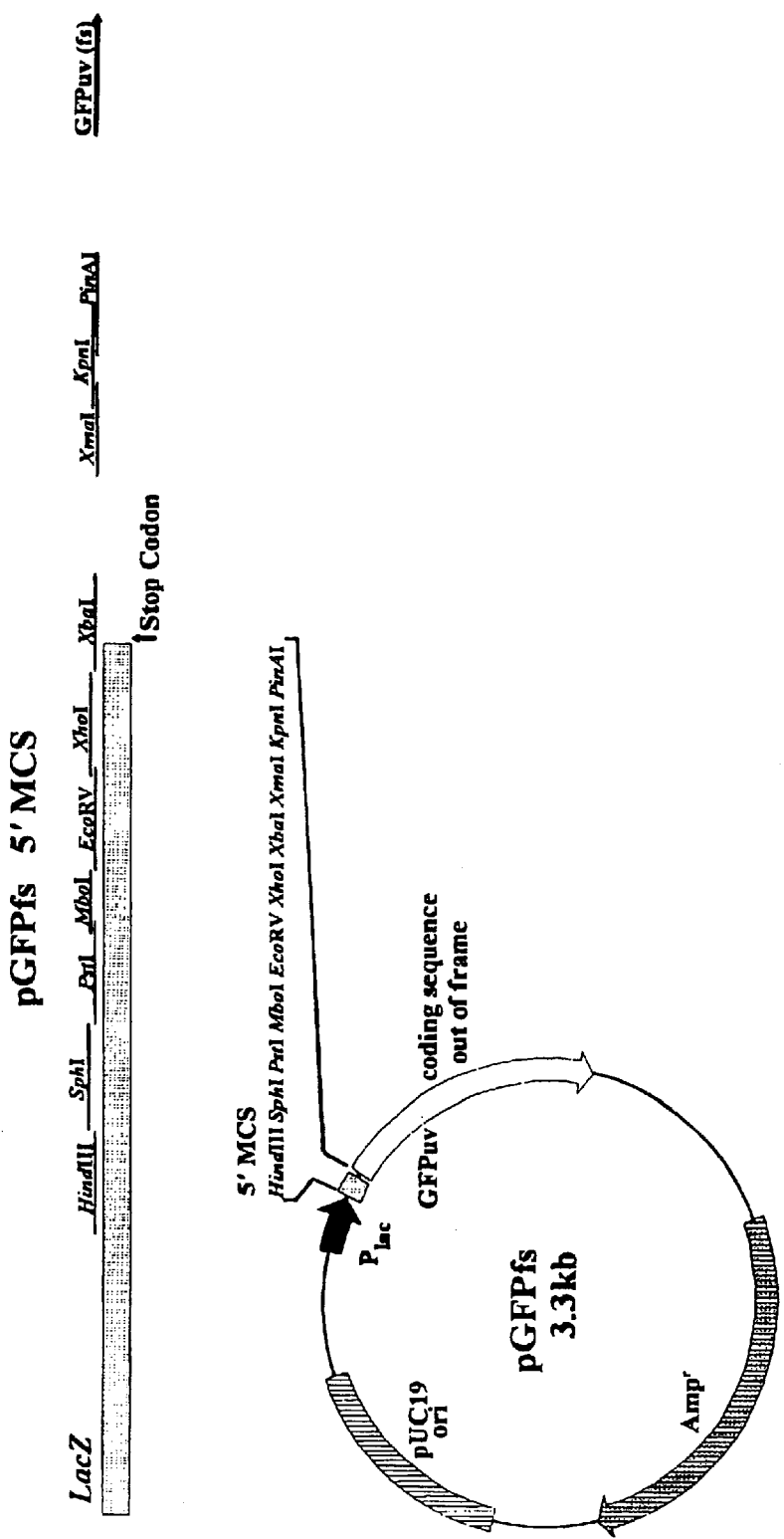
FIG. 1 is a schematic illustration of the DNA vector as disclosed in the present invention including the engineered indicator sequence and restriction sites creating an out-of-reading-frame sequence.

The present invention provides a DNA expression vector for positively selecting out-of-reading-frame mutations including frameshifts and stop codons in DNA sequences which need to be tested for frameshifts and/or stop codons. The vector is engineered to include a promotor operatively linked to an expressible reporter gene through a linkage sequence. The linkage sequence includes at least two restriction sites and an engineered frameshift.

The reporter gene is engineered as known in the art to be expressible and produce a product when the coding sequence is in-frame. The reporter gene can be a chimeric gene.

In an embodiment as described herein in the Example, the reporter gene product is expressed as a fusion product including a green fluorescent protein (GFP; Kain et al., 1995; Cha;foe et al., 1994; U.S. Pat. Nos. 5,491,084; 5,422, 266 5,162,227). The linkage sequence includes at least two restriction sites and an engineered frameshift. In an embodiment the frameshift is established by the partially complementary oligonucleotides: 5'-GATCGATATCTCGAGT-3' (SEQ ID No:1) and 5'-CTAGACTCGAGATATCGATCTGCA-3' (SEQ ID No:2).

The DNA expression vector of the present invention was derived from the pGFPuv™ produced by Clontech, Inc., Palo Alto, Calif. pGFPuv™ carries the "cycle 3" variant for the Green Fluorescent Protein (GFP) reporter gene (Crameri, et al., 1995). This gene was cloned into the multiple cloning site of the pUC19 derivative pPD16.43, which also contained an ampicillin resistance gene (Fire, et al., 1990). The GFP gene was inserted in-frame with the lacZ initiation codon from pUC19 to form a chimeric reporter gene sequence so that β-galactosidase-GFP chimeric protein is expressed from the lac promoter in E. coli. The GFP variant in this vector differs from wild type GFP in that it is optimized for bacterial expression, solubility, and fluorescence of the IPTG inducible lacZ:GFPuv fusion protein allowing propagation of vector transformed E. coli in the presence of the antibiotic.

By operatively linked through the linkage sequence, it is meant that the promotor must initiate translation of the reporter gene and the linkage sequence, with the linkage sequence being initiated first. The promotor is positioned such that it will not initiate translation only of the reporter gene. In the vector of the present invention, the linkage sequence is inserted within the reporter gene, in this embodiment a chimeric GFPuv. However, the linkage sequence can be inserted in the vector in any position that requires that the promotor specifically initiate transcription of the linkage sequence before the reporter gene.

The DNA sequence to be tested for frameshifts and/or stop codons is cloned into the vector. The primers are designed to accommodate the insertion point in the linker sequence. Multiple restriction sites are provided so as to allow three protocols for insertion of the DNA sequence to be tested. In the first type, the engineered frameshift in the linkage sequence is removed by using restriction sites that are 5' and 3' to the frameshift. If the sequence being tested maintains the continuity of the open reading frame of the reporter gene, then the reporter product is made. In the second type, the 3' primer provides the necessary nucleotides to correct the frameshift and thereby provide an open reading frame and production of reporter product. For example, primers designed to either remove the frameshift (HindIII/KpnI cloning) or primers designed to introduce a second complementary frameshift within the 3' primer (e.g., HindIII/PstI cloning) would reestablish the correct reading frame and allow expression of GFPuv.

In the third type, the DNA sequence to be tested is inserted upstream, 5', from the engineered frameshift in the linkage sequence. If the DNA sequence being tested contains a 3' frameshift that is complementary to the engineered frameshift, then the reading frame is corrected and reporter product is made.

It should be noted that the selection of GFP in the reporter gene allows for these insertion protocols as it is not generally affected by the presence of the DNA sequence to be tested. GFP is unique among light emitting proteins that is does not require cofactors as substrates and is therefore autofluorescent and is stable (Chalfie, et al., 1994; Mioteli and Spector, 1997; Yang et al., 1996) in that the fluorescence is not quenched by changes in pH and temperature.

Figure 2:
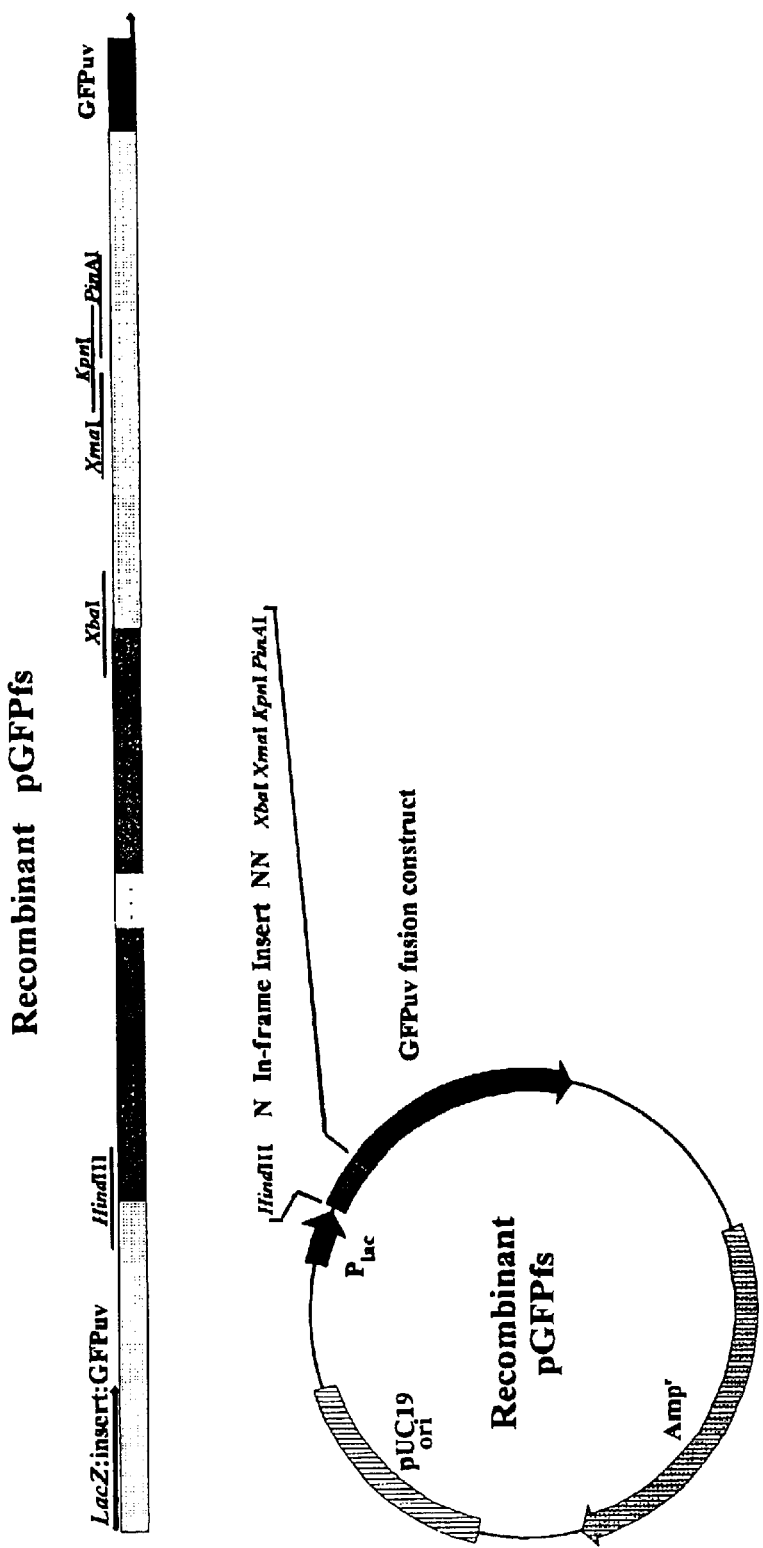
FIG. 2 is a schematic illustration of the DNA vector with an insert that has restored the reading frame.

Because cloning sites are 5' of the GFPuv coding sequence, expression of GFPuv requires frame continuity within an insert. Therefore, directional cloning of PCR-derived products that are devoid of stop codons can be used to correct the reading frame to that of the GFPuv coding sequence (FIG. 2). Primers incorporating restriction sites can be designed to either remove the frameshift (e.g., HindIII/KpnI cloning) or to introduce a second frameshift within the 3' primer (e.g., HindIII/PstI cloning). These frameshifts can reestablish the correct reading frame. Alternatively, as described herein, a frameshift being screened for within the sequence to be tested may also be used to reestablish the correct reading frame which can be used in population screenings.

The promotor for controlling transcription of the heterologous material can be either a constitutive or inducible promotor to allow selective transcription. In the preferred embodiment, an IPTG inducible LacZ promoter is used. The vectors can also contain elements for use in either procaryotic or eucaryotic host systems. One of ordinary skill in the art will know which host systems are compatible with a particular vector. Both the promotor and reporter gene will be selected to be compatible with the host system. A particular host system will be utilized and selection will include considerations of the gene or DNA sample that is being evaluated for an out-of-reading-frame mutation and what host system will best accommodate the genetic material for analysis. The product of reporter genes can be measured as is known in the art depending on their product using appropriate immunoassays, enzyme assays, calorimetric assays or fluorescence upon UW exposure.

The present invention further provides a method to evaluate PCR products for amplification artifacts using the vector of the present invention. As discussed herein, during PCR errors and amplification artifacts can occur. These artifacts can be errant priming, frameshifts and replaced nucleotide such that the resulting codon is a stop codon. In the method, the PCR product is cloned into the DNA expression vector. For general evaluation, the engineered frameshift is removed using a primer set such that restriction sites that were selected result in removal of the engineered out-of-reading-frame mutation or the primers provide a correction to the engineered frameshift to create an open reading frame. Either approach can be used. Factors such as the size of the PCR product to be tested may or may not need to be evaluated as are known to those skilled in the art.

After transformation the *E. coli* is induced to produce the reporter product, in the embodiment with the vector of the present invention it is a fusion product including GFP as described herein. If the GFP is present, then the PCR product does not contain a frameshift or stop codon. If no GFP is present, the PCR product can be further analyzed by sequencing.

The vector can be utilized in scanning or screening extended multigene families for the presence of previously unrecognized frameshift mutations or for known ones in a population screening for people at risk. In addition, pGFPfs cloning can be used to identify out-of-frame sequences, such as those arising from disease-causing mutations. For a screening application, which could serve as a primary diagnostic tool, amplifications are carried out under highly stringent conditions using primers that are designed to require a frameshift (associated with disease) immediately upstream of the 3' primer to rescue GFP expression; amplification of the corresponding normal (i.e., wildtype) sequence would therefore not rescue GFP expression. In such an application, the engineered frameshift is designed to be complementary to the disease-associated frameshift that is being screened for in the population so that the disease-associated frameshift's presence in the sequence being tested will correct the reading frame.

In general, pGFPfs is a convenient, highly efficient tool for distinguishing in-frame from out-of-frame and/or termination codon-containing sequences and has potential application for distinguishing wild-type and certain mutant sequences.

The above discussion provides a factual basis for the vector and use of vector of the present invention. The methods used with and the utility of the present invention can be shown by the following non-limiting examples and accompanying figures.

EXAMPLES

General Methods

General methods in molecular biology: Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA, Scientific American Books*, New York and in Birren et al (eds) *Genome Analysis: A Laboratory Manual Series*, Vols. 1–4 Cold Spring Harbor Laboratory Press, New York (1998) and methodology as set forth in U.S. Pat. Nos. 4,666,828; 4,683,202; 4,801,531; 5,192,659 and 5,272,057; 5,538,885 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.).

Immunoassays: ELISAs are one type of immunoassay employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, N.Y., 1989.

Vector Design and Testing

To facilitate identification of PCR amplification products containing open reading frames or stop codons and also to screen for out-of-reading-frame mutations in a candidate gene in a patient, a vector, pGFPfs, was engineered that affords positive selection of recombinants based on the continuity of coding sequence within a lacZ:insert:GFP (green fluorescent protein) fusion construct that is expressed in *E. coli* and does not require subjective assesment.

pGFPfs was derived from pGFPuv™ (CLONTECH Laboratories, Palo Alto, Calif., USA) by ligating a linker (formed by annealing the partially complementary oligonucleotides: 5'-GATCGATATCTCGAGT-3' (SEQ ID No:1) and 5'-CTAGACTCGAGATATCGATCTGCA-3' (SEQ ID No:2) into the multiple cloning site (MCS) of PstI/XbaI-digested pGFPuv. Incorporation of this linker, which was confirmed by DNA sequencing, disrupts the GFPuv reading frame and introduces additional unique restriction sites (FIG. 1). The GFP variant in these vectors, GFPuv, differs from wild-type GFP (Prasher et al, 1992) in that it is optimized for bacterial expression, solubility and fluorescence of the isopropyl-β-D-thiogalactopyrano-side (IPTG)-inducible lacZ:GFPuv fusion protein (Crameri et el, 1996).

Colonies producing GFPuv fusion proteins are easily identified by viewing under longwave UV light. Positive selection of recombinants containing in-frame inserts is based on correction of a frameshift that has been engineered within the 5' MCS of pGFPfs as described herein above.

For testing PCR products were generated using previously described methods (Rast et al., 1997, 1995, 1994) and were ligated into HindIII/XbaI-digested pGFPfs. Ligation mixtures were used to transfect E. coli DH5αF™ (Life Technologies, Gaithersburg, Md., USA). Cells were plated on LB plates containing 10 mM IPTG and 100 ug/mL ampicillin, and colonies were grown at 30° C. for 48 hours. Plates were viewed using a UVL 56 Blak-Rays® (366 nm) longwave ultraviolet lamp (UVP, Upland, Calif., USA).

Plasmid DNA was isolated for sequencing using a QIAprep® Spin Miniprep Kit (Qiagen, Chatsworth, Calif., USA) in accordance with the manufacturer's recommended protocol. Sequencing was performed with a 4000 L Automated Sequencer (LI-COR, Lincoln, Nebr., USA) using a SequiTherm™ Long-Readt™ Cycle Sequencing Kit (Epicentre Technologies, Madison, Wis., USA).

IPTG induction of the engineered pGFPfs of the present invention generates a 17-amino acid protein that is encoded by a fragment of lacZ, the contiguous cloning sites and a 3' termination codon (FIG. 1); GFPuv is not expressed. Because cloning sites are 5' of the GFPuv coding sequence, expression of GFPuv requires frame continuity within an insert. Therefore, directional cloning of PCR-derived products that are devoid of stop codons can be used to correct the reading frame to that of the GFPuv coding sequence (FIG. 2). Primers incorporating restriction sites can be designed to either remove the frameshift (e.g., HindIII/KpnI cloning) to introduce a second frameshift within the 3' primer (e.g., HindIII/PstI closing) to reestablish the correct reading frame and allow expression of GFPuv and as described herein above the frameshift being screened may also reestablish the correct reading frame.

The capacity of pGFPfs to discriminate between coding and noncoding amplification products is dependent on noncoding products having an internal stop codon(s) or shifted reading frame; i.e., ±1 base. It is apparent that 66% of noncoding products will not have the correct number of nucleotides needed to restore the GFP coding sequence. However, the variable prevalence of stop codons in PCR-derived products provides an additional basis for exclusion of noncoding recombinants.

Validation studies of the pGFPfs construct were carried out initially by (re)amplification of previously characterized in-frame and out-of-frame single-strand M13 templates, derived in the course of earlier studies (Rast et al., 1994). Sequencing of templates recovered from isolated nonfluorescent colonies transfected with pGFPfs or recombinant pGFPfs containing out-of-frame inserts as well as from fluorescent colonies transfected with recombinant pGFPfs-containing inserts with continuous reading frames confirmed the correlation (100%) of fluorescence with in-frame sequences. Cloning of products derived by amplification with short, minimally degenerate primers using total mRNA-derived cDNA as template yields GFP-expressing recombinants, nonexpressing recombinants and uncut vector. False-positive colonies have been observed and typically are the result of the integration of short inserts lacking termination codons that could not be eliminated by size selection. The generation of such interfering amplifications correlates directly with decreased primer stringency and/or template heterogeneity.

In experiments using total mRNA-derived cDNA as template, undesired in-frame recombinants represent less than 15% of positives. Based on experience with conventional M13 cloning and sequencing of short primer amplification products (in excess of 1000 analyses), less than 15% of recombinants represent in-frame sequences (Rast et al., 1997, 1995, 1994). The use of pGFPfs cloning from total mRNA-derived cDNA resulted in a 5–6-fold overall improvement in the efficiency of identification of both known and novel in-frame sequences (Table 1). In-frame inserts of >800 bp have been shown to produce detectable GFPuv fusion proteins.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

| pGFPfs CLONING | | |
|---|---|---|
| Sequencing Events* | green fluorescent colonies | 37 |
| Desirable Products | in-frame (ca. 200 bp) | 31 |
| Undesirable Products | in-frame artifacts (45–129 bP) | 5 |
|  | out-of-frame (stop codon) | 1 |
| Efficiency | (31/37) 84% | |

*As controls, 15 GFPuv-nonexpressing (white) colonies were recovered and determined to be out-of-frame artifacts or vector.

REFERENCES

Bozdech, et al., 1996. Cloning and sequence analysis of a novel member of the ATP-binding cassette (ABC) protein gene family from *Plasmodium falciparum*. Mol. Biochem. Parasitol. 81:41–51.

Chalfie, et al., 1994. Green Fluorescent Protein as a Marker for Gene Expression. Science 263:802–805.

Claverie, 1995. Detecting Frame Shifts by Amino Acid Sequence Comparison. J. Mol. Biol. 234:1140–1157.

Crameri, et al., 1996. Improved green fluorescent protein by molecular evolution using DNA shuffling. Nat. Biotechnol. 14:315–319.

Fichant and Quentin, 1995. A frameshift error detection algorithm for DNA sequencing projects. Nucleic Acid Res 23(15):2900–2908.

Fire, et al., 1990. A modular set of lacZ fusion vectors for studying gene expression in *Caenorhabditis elegans*. Gene 93:198–198.

Hardy and Duff, 1993. Heterogeneity in Alzheimer's Disease. Ann.Med. 25:437–440.

Hawke et al., 1996. Improvements in short primer PCR based identification of novel IgSF members. Suncoast Biomolecular Science Conference, 34, Abstract P-2.

Kain et al., 1995. Green Fluorescent Protein as a Reporter of Gene Expression and Protein Localization. BioTechniques 19:650–655.

Kahn et al., 1995. Design of a selectable reporter for the detection of mutations in mammalian simple repeat sequences. Carcinogenesis 16(5):1223–1228.

Kim, et al., 1996. Characterization of the PEST family protein tyrosine phosphatase BDP1. Oncogene 13:2275–2279.

Marwood, et al., 1995. *Escherichia coli* lacZ strains engineered for detection of frameshift mutations induced by aromatic amines and nitroaromatic compounds. Carcinogenesis 16(9):2037–2043.

Misteli and Spector, 1997. Applications of the green fluorescent protein in cell biology and biotechnology. Nature Biotechnology 15:961–964.

Partula, et al., 1995. Structure and diversity of the T cell antigen receptor β-chain in a teleost fish. J. Immunol. 155:699–706.

Prasher, et al., 1992. Primary structure of the Aequorea victoria green-fluorescent protein. Gene 111:229–233.

Rast, et al., 1997. αβ, γ, and δ T cell antigen receptor genes arose early in vertebrate phylogeny. Immunity 5:1–11.

Rast, et al., 1995. Identification and characterization of T-cell antigen receptor related genes in phylogenetically diverse vertebrate species. Immunogenetics 42:204–212.

Rast and Litman, 1994. T cell receptor gene homologs are present in the most primitive jawed vertebrates. Proc. Natl. Acad. Sci. USA 91:9248–9252.

Yang et al., 1996. The molecular structure of green fluorescent protein. Nature Biotechnology 14:1246–1251.

Yoshihara, et al., 1994. BIG-1: a new TAG-1/F3-related member of the immunoglobulin superfamily with neurite outgrowth-promoting activity. Neuron 13:415–426.

Varesco, et al., 1993. A rapid screening method to detect nonsense and frameshift mutations: Identification of Disease-causing APC Alleles. Cancer Research 53:5581–5584.

Fodor et al, "Multiplexed biochemical assays with biological chips", *Nature* 364:555–556 (1993).

Kawasaki E S. Amplification of RNA. In: PCR protocols: A Guide to Methods and Applications, Innis M A, Gelfand D H, Sninsky J J, White T J, eds. Academic Press, 1990, pp21–27.

Lichter et al., "High-resolution mapping of human chromosome 11 by in situ hybridization with cosmid clones-"*Science* 247:64–69 (1990).

Orita et al. Detection of polymorphisms of human DNA by gel electrophoresis as single-strand conformation polymorphisms. Proc Natl Acad Sci USA 1989; 86:2766–2770.

Pease et al., "Light-generated oligonucleotide arrays for rapid DNA sequence analysis", *Proc. Natl. Acad. Sci. USA* 91(11):5022–5026 (1994).

Testoni et al., 1996. Blood 87:3822.

What is claimed is:

1. A DNA expression vector for positively selecting out-of-reading-frame mutations comprising a promotor operatively linked to an expressible reporter gene through a linkage sequence wherein said linkage sequence includes at least two restriction sites and an engineered frameshift mutation and wherein said expressible reporter gene when appropriately expressed provides a fusion product including a green fluorescent protein for positively selecting unknown out-of-reading-frame mutations.

2. A DNA expression vector for positively selecting out-of-reading-frame mutations comprising a promotor operatively linked to an expressible reporter gene through a linkage sequence wherein said linkage sequence includes at least two restriction sites and an engineered frameshift mutation which is established by complementary sequences SEQ ID Nos: 1 and 2 and wherein said expressible reporter gene when appropriately expressed provides a fusion product including a green fluorescent protein for positively selecting unknown out-of-reading-frame mutations.

3. The vector as set forth in claim 1 wherein said restriction sites are selected from the group consisting of HindIII, Xbal, PstI, Xhol, and Xmal.

4. The vector as set forth in claim 1 wherein said promoter is lacZ and inducible in *E. coli*.

5. The vector as set forth in claim 1 wherein said linkage sequence is inserted within the reporter gene sequence.

6. A method to evaluate PCR products for amplification artifacts including the steps of cloning the PCR product test sequence into the DNA expression vector as set forth in claim 1 with a designed primer set such that restriction sites are selected resulting in removal of the engineered out-of-reading-frame mutation, transforming a microorganism with the recombinant DNA vector;

inducing expression of the reporter gene; and assaying for the presence of the reporter product fusion protein including a green fluorescent protein produced from this expression whereby if there is not a frameshift or stop codon in the PCR product test sequence the reporter product is made.

7. The method as set forth in claim 6 including the step of engineering the primer set to provide a correction for the engineered out-of-reading-frame mutation and correcting the reading frame upon insertion of the PCR product test sequence for evaluation 5' of said engineered frameshift and whereby if there is not a frameshift or stop codon in the PCR product test sequence the reporter product is made.

8. The method as set forth in claim 6 including the step of engineering the primer set only to insert the PCR product test sequence for evaluation wherein if the reporter product is made, the reading frame has been corrected by a frameshift error in the PCR product test sequence that is complementary to the engineered frameshift mutation in the linkage sequence of said vector.

* * * * *